(12) United States Patent
Brand et al.

(10) Patent No.: US 8,377,876 B2
(45) Date of Patent: Feb. 19, 2013

(54) PEDIATRIC AMINO ACID SOLUTION FOR PARENTERAL NUTRITION

(75) Inventors: Ortrud Brand, Ostfildern (DE); Thorsten Erbe, Butzbach (DE); Georg Achleitner, Graz (AT); Norbert Feichtinger, Graz (AT)

(73) Assignee: Fresenius Kabi Deutschland GmbH, Bad Homburg v.d. H. (DE)

( * ) Notice: Subject to any disclaimer, the term of this patent is extended or adjusted under 35 U.S.C. 154(b) by 873 days.

(21) Appl. No.: 12/226,358

(22) PCT Filed: Mar. 5, 2007

(86) PCT No.: PCT/EP2007/001878
§ 371 (c)(1),
(2), (4) Date: Nov. 21, 2008

(87) PCT Pub. No.: WO2007/121807
PCT Pub. Date: Nov. 1, 2007

(65) Prior Publication Data
US 2009/0203626 A1    Aug. 13, 2009

(30) Foreign Application Priority Data

Apr. 20, 2006 (DE) .......................... 10 2006 018 293

(51) Int. Cl.
*A61K 38/02* (2006.01)
*A61K 38/05* (2006.01)
(52) U.S. Cl. ...................... 514/5.5; 514/21.9; 514/21.91
(58) Field of Classification Search ................... 514/5.5, 514/21.9, 21.91
See application file for complete search history.

(56) References Cited

U.S. PATENT DOCUMENTS

| | | | | |
|---|---|---|---|---|
| 5,206,220 A | * | 4/1993 | Hilton | 514/5.5 |
| 5,432,160 A | * | 7/1995 | Hara et al. | 514/5.5 |
| 5,438,042 A | * | 8/1995 | Schmidl et al. | 514/5.5 |
| 5,504,072 A | | 4/1996 | Schmidl et al. | |
| 5,607,975 A | * | 3/1997 | Smith et al. | 514/563 |
| 5,719,134 A | * | 2/1998 | Schmidl et al. | 514/58 |
| 6,080,788 A | * | 6/2000 | Sole et al. | 514/561 |

FOREIGN PATENT DOCUMENTS

| | | |
|---|---|---|
| CA | 2134380 | * 10/1994 |
| EP | 1 065 947 B1 | 1/2001 |
| WO | WO 91/16067 A1 | 10/1991 |

OTHER PUBLICATIONS

Abstract of Furst EP 0087750, Sep. 1983.*
Fürst, P. "New Developments in Glutamine Delivery", *The Journal of Nutrition*, (2001), vol. 131, No. 9 (Suppl.), pp. 2562S-2568S, American Society for Nutrional Science.
Fürst, P. "New Developments in Glutamine Delivery", *The Journal of Nutrition*, (2001), vol. 131, No. 9 (Suppl.), pp. 2562S-2568S, American Society for Nutritional Science.
Fürst, P. et al. "Amino-Acid Substrates in New Bottles: Implications for Clinical Nutrition in the $21^{st}$ Century", *Nutrition* (2000), vol. 16, Nos. 7/8, pp. 603-606.
Haynes, T.E. et al. Glutamine prevents hydrogen peroxide-induced enterocyte death. FASEB Journal (2004), vol. 18, p. A476, Abstr. 339.5.
Kalhan, S.C. et al. Glutamine Supplement with Parenteral Nutrition Decreases Whole Body Proteolysis in Low Birth Weight Infants, (2005), vol. 146, pp. 642-647, The Journal of Pediatrics.

* cited by examiner

*Primary Examiner* — David Lukton
(74) *Attorney, Agent, or Firm* — Nath, Goldberg & Meyer; Tanya E. Harkins

(57) ABSTRACT

The present invention relates to an amino acid solution for the parenteral nutrition of pediatric patients. The amino acid solution provides for an increased concentration of glutamine, tyrosine, cysteine and taurine, while the concentrations of phenylalanine and methionine is small. Glutamine and tyrosine are provided in the form of oligopeptides.

16 Claims, No Drawings

US 8,377,876 B2

PEDIATRIC AMINO ACID SOLUTION FOR PARENTERAL NUTRITION

This application is a 371 of PCT/EP2007/001878, filed Mar. 5, 2007, which claims foreign priority to DE 102006018293.6, filed Apr. 20, 2006.

The invention relates to an amino acid solution for parenteral nutrition comprising amino acids according to the preamble of claim 1. The solution is suitable in particular for parenteral nutrition of premature infants and neonates, babies and small children, either as parenteral supplement or in combination with other nutrient solutions as total parenteral nutrition (TPN). The invention further relates to a method for preparing said amino acid solutions.

If complete nutrition cannot be ensured by the oral/enteral route, a complete or additional parenteral nutritional therapy is indicated. In this case, the food is taken in by the intravenous route. This is necessary in particular when there is an obstruction of the gastrointestinal tract. Malformations or inflammations of the bowel frequently occur in premature infants and neonates, babies and small children. Examples thereof are inflammatory bowel disorders such as Crohn's disease, ulcerative colitis etc., and gastrointestinal fistulas, malignant bowel disorders, short-bowel syndrome or inadequate development of the bowel at the time of birth. Parenteral nutrition may additionally be indicated in the perioperative area, in intensive care patients, in cases of sepsis or therapy-resistant diarrhea.

A suitable amino acid solution for babies and small children differs greatly in the requirements for the amino acid pattern from amino acid solutions for adults. Based on body weight, small children require distinctly more amino acids. A small child's metabolism likewise differs from that of an adult. Various amino acids which are regarded as non-essential for adults must be regarded as essential for premature infants and neonates and for small children because the body is able itself to synthesize these amino acids in adequate amounts only above a certain age. Although other amino acids can be synthesized even by the small child, this takes place at a slower rate than is the case in adults. It is therefore possible on use of an amino acid solution designed for adults, when employed for premature infants and neonates, and small children, for there to be signs of deficiency and/or excess of particular amino acids. This is the case in particular for the amino acids glutamine, tyrosine, cysteine, taurine, methionine and phenylalanine.

Because amino acid metabolism is not yet fully developed in particular in premature infants and neonates, the balance of the mixture is particularly important because compensation for any irregularities is more difficult for the young body. A precise and continuous parenteral nutrition must furthermore be regarded as particularly important for premature infants and neonates and for small children when required, because the body has not yet built up its own definite reserves through which the possible signs of deficiency could be alleviated. Only at an age of >2 years does children's metabolism start to approach that of adults. Although the amino acid solution of the invention is specifically adapted for the needs of pediatric patients, use for adults, in whom similar signs of deficiency may occur owing to pathophysiological alterations in metabolism, is also conceivable. This is the case in particular for patients with renal or hepatic disorders.

It is therefore indispensable to redefine, taking account of a wide variety of criteria as described in detail hereinafter, the amino acid pattern for an amino acid solution for parenteral nutrition of premature infants and neonates, and small children. Crucial in this connection is not only the amount of the individual amino acids but also the mode of administration and a good technological transfer in the preparation of the solution; this applies particularly to the sterilization conditions.

EP 0 148 680 A1 describes an amino acid solution which is suited to pediatric requirements for parenteral nutrition. The amino acids cysteine, taurine and tyrosine are characterized as semi-essential.

DE 2531201 A1 shows how an appropriate nitrogen balance can be obtained with parenteral pediatric amino acid solutions. There is also a discussion of the advantages of administering adapted amounts of free amino acids compared with administering protein hydrolysates.

WO91/16067 A1 describes the use of oligopeptides for a parenteral nutrition solution which can be employed for pediatric purposes.

The general use of oligopeptides, especially tri-and dipeptides, for amino acid solutions for parenteral nutrition and the beneficial effects associated therewith for solubility and product stability are discussed in U.S. Pat. No. 5,432,160, DE 31 08 079 C2, EP 0 087 751 A1 and EP 0 087 750 B1.

None of the aforementioned publications reveals that it is possible by using oligopeptides for providing amino acids to administer amounts of particular amino acids which are at a level other than that previously described but are better suited for the development of the neonatal body.

The invention is therefore based on the object of providing an amino acid solution for parenteral nutrition which has an amino acid pattern which is specifically suited to the needs of premature infants and neonates, babies and small children and which provides all the amino acids required in adequate amount and ratio. Particular attention is directed in this connection to the provision of appropriate amounts of the amino acids glutamine, tyrosine, cysteine and taurine in easily metabolizable form, and to the reduction, associated therewith, of the amino acids glutamic acid, phenylalanine and methionine.

The object is achieved by providing an amino acid solution for parenteral nutrition of pediatric patients as claimed in claim 1 and the use in claim 13.

A further object of the invention relates to the provision of a complete parenteral nutrition which provides all the required amino acids in adequate amount and ratio.

The object is achieved by providing a medicinal composition that is an amino acid solution for parenteral nutrition of pediatric patients, characterized in that the amino acid solution comprises 9-30 g glutamine per 100 g of amino acids and 0.3-2 g taurine per 100 g of amino acids, which provides for a) 30-60% of the energy by carbohydrates, b) 30-50% of the energy by fats, c) 10-20% of the energy and the use thereof for the preparation of a parenteral infusion solution for the treatment of pediatric patients, characterized in that the infusion solution comprising a daily dose of 90-180 kcal/kg body weight of the patient.

A further object which relates to the optimization of the method of sterilization of a parenteral infusion solution for the treatment of pediatric patients, characterized in that the infusion solution comprising a daily dose of 90-180 kcal/kg body weight of the patient.

Advantageous embodiments are indicated in the dependent claims.

Depending on the body weight and state of development of the premature infant and neonate, a volume of 100-160 ml per kg of body weight (BW) and day should not be exceeded in the parenteral nutrition. In order on the one hand to avoid local excessive concentrations on administration, but on the other hand to ensure miscibility with other components such as solutions of carbohydrates, fats, electrolytes, vitamins and trace elements without in this way exceeding the volume limit, the amino acid solution comprises 3-30% w/w protein building blocks, preferably 5-20% w/w protein building blocks and particularly preferably 7-15% w/w protein building blocks. The protein building blocks are preferably in the form of free amino acids, di-or tripeptides, and the content of peptides with a chain length of >5 or proteins is less than 5% of the protein building blocks, preferably less than 1%.

The amino acid solution for parenteral nutrition of premature infants and neonates, babies and small children differs from usual amino acid solutions for parenteral nutrition of adults in the quantitative content and the amino acid pattern.

In contrast to adults in whom, at a constant weight, the synthesis and breakdown of proteins are approximately in balance, it is necessary for synthesis distinctly to predominate in premature infants and neonates and in small children because of the rapid growth of body mass. For this reason, the daily requirement for amino acids in these patients is distinctly increased by comparison with adults based on body weight. The daily dose of the protein building blocks administered by the amino acid solution is 2-4 g, preferably 2.5-3.5 g, per kilogram of body weight in order to meet the total daily requirement of the pediatric patient. An amount of 3 g of protein building blocks per kilogram of body weight is used for normal calculations.

All the indicated amino acids can be provided in free form or in the form of their precursors. If the amino acids are to be provided in the form of their precursors, the stated amounts for the amino acids relate only to the amino acid portion of the precursors. Levorotatory amino acids are preferably employed in all cases.

Besides an increased daily requirement of premature infants and neonates, and small children, however, their metabolism differs in a particular way from that of adults since various amino acids are formed and/or degraded at a reduced rate by comparison. Some amino acids which are endogenously synthesized in adults, and are thus regarded as non-essential, cannot be adequately formed endogenously by premature infants and neonates, and by small children, and must therefore be regarded as essential or semi-essential in these cases. These amino acids, supply of which is therefore particularly important, are cysteine, tyrosine, glutamine and taurine. Other amino acids are degraded only at a reduced rate by premature infants and neonates, and small children, including phenylalanine and methionine.

Glutamine is the most commonly occurring amino acid. It occurs in large amounts in plasma and in muscles. Glutamine is to be regarded as indispensable, especially for cells with a high mitosis rate. These include for example cells such as lymphocytes and enterocytes. An adequate supply of glutamine thus also ensures inter alia a functioning immune system. Glutamine is moreover essential for the construction and maintenance of muscle mass. Since the neonatal body cannot itself produce glutamine in sufficient amount, an appropriate supply of this amino acid during parenteral nutrition is particularly important. This also applies in relation to the synthesis of purines and pyrimidines. Glutamine is a precursor of these DNA building blocks. Glutamine is therefore particularly important in the growing body of a premature infant and neonate and of a small child where cell division frequently occurs. Besides which, glutamine is a precursor of glutathione which plays an important role as antioxidant.

For these reasons, the parenteral composition of the invention comprises an increased proportion of glutamine which amounts to 9-30 g, preferably 11-25 g and particularly preferably 13-20 g of glutamine per 100 g of amino acids (AA). The daily dose of glutamine employed per kilogram of body weight is 0.25-0.90 g, preferably 0.3-0.75 g and particularly preferably 0.39-0.6 g.

A further amino acid which is regarded as non-essential for adults, tyrosine, must be considered at least to some extent as an essential amino acid in premature infants and neonates, and small children. The ability of the neonatal body to synthesize tyrosine from phenylalanine is only very limited or nonexistent. The reason is the deficient expression of the enzyme responsible therefor, phenylalanine hydroxylase. As a consequence thereof, at the same time the breakdown of phenylalanine is reduced by comparison with the adult body. Besides the general function as building block for constructing proteins, tyrosine is a precursor of norepinephrine, dopamine, thyroxine and further hormones. An adequate supply of tyrosine is therefore of very great importance for a controlled hormone balance and for the structure of the nervous system.

For these reasons, the parenteral composition comprises an increased proportion of readily metabolizable tyrosine, which amounts to 1-4 g, preferably 1.2-3 g and particularly preferably 1.5-2.5 g of tyrosine per 100 g of amino acids. The daily dose of tyrosine employed per kilogram of body weight is 30-120 mg, preferably 35-90 mg and particularly preferably 45-75 mg.

Tyrosine and phenylalanine compete with one another for their transport pathways into the tissue. An elevated phenylalanine level thus inhibits the uptake of tyrosine. Because of the reduced breakdown of phenylalanine on the one hand, and on the other hand in order to keep the total amount of aromatic amino acids constant in relation to the other amino acids (AA), the amount of phenylalanine in the amino acid solution of the invention is reduced. The total amount of aromatic amino acids should not exceed 7 g/100 g of AA, preferably 6 g/100 g of AA and particularly preferably 5.6 g/100 g of AA.

The parenteral composition comprises 3-5 g/100 g of AA, preferably 3.3-4 g/100 g of AA and particularly preferably 3.5-3.8 g/100 g of AA phenylalanine. The ratio of tyrosine to phenylalanine is 1:1 to 1:3, preferably 1:1.3 to 1:2.5 and particularly preferably 1:1.5 to 1:2.

Because of the low activity of the enzymes cysteinesulfinate decarboxylase and cystathionase, the transsulfuration metabolism in premature infants, neonates and small children is scarcely detectable. The synthesis of cysteine from methionine, and of taurine from cysteine, therefore takes place at only very low rates or not at all. Both cysteine and taurine are therefore to be regarded as essential for the neonatal body. However, taurine in particular plays an important role in the development of premature infants and neonates, and small children, for the development of the central nervous system, the digestive system, vision and hearing, and the calcium balance in cells in general and nerve cells in particular. Besides the function as protein building block, cysteine likewise acts as precursor of the tripeptide glutathione which plays an important role in preventing oxidative stress. It has emerged that large amounts of taurine are readily accepted by the neonatal body even by comparison with doses hitherto customary.

For this reason, the relative amounts of cysteine and taurine in the composition are increased, whereas the amount of methionine is reduced. The total amount of cysteine, taurine and methionine does not exceed 5 g/100 g of AA, but is at least 2 g/100 g of AA.

The composition comprises 0.3-1.5 g of cysteine/100 g of AA, preferably 0.5-1 g/100 g of AA. The composition further comprises 0.3-2 g of taurine/100 g of AA, preferably 0.7-1.5 g/100 g of AA.

Since cysteine is unstable as free amino acid in aqueous solutions and, in particular, does not permit thermal sterilization, cysteine is preferably employed in the form of the precursor N-acetyl-L-cysteine. Administration in the form of other precursors, especially in the form of oligopeptides, is likewise possible within the scope of the invention.

The preparation of amino acid solutions comprising glutamine and tyrosine in appropriate amounts has not been possible without the use of the stable and readily soluble oligopeptides. The solubility of both free amino acids is low. In addition, the use of free glutamine does not allow thermal sterilization. For this reason, glutamic acid has often in the past been employed as glutamine substitute. Glutamic acid and glutamine are in a metabolic equilibrium in the body, but endogenous interconversion thereof is possible to only a certain extent. Glutamic acid therefore cannot be regarded as a complete glutamine substitute. It has been found that administration of large amounts of glutamic acid has excitatory effects and brings about an overactivity in the stimulation of nerve cells, possibly leading to cell deaths [Barinaga (1990) Science 247:20-22]. In contrast thereto, it has been possible to find that administration of increased amounts of glutamine is not harmful. In addition, the daily dose required of glutamic acid can certainly be covered by an increased intake of glutamine. An appropriate parenteral nutrition is thus also possible in the complete absence of glutamic acid if the basic supply is ensured by appropriately high doses of glutamine. For this reason, the proportionate amounts of glutamine in the composition of the invention also distinctly exceed amounts used hitherto.

The stability and solubility problem is solved by providing glutamine in the form of an oligopeptide, in particular of a tri-or dipeptide. Examples of tripeptides are X'-Gln-X, X'-X-Gln and Gln-X'-X. Examples of dipeptides are Gln-X and X-Gln. X and X' are any naturally occurring amino acids, and alanine and glycine are preferably used.

The free amino acid tyrosine likewise has the disadvantage of low solubility. The low solubility of tyrosine has led in the past to the necessity to prepare amino acid solutions in a lower total concentration than the ideal of about 10% w/w protein building blocks (7-15% w/w protein building blocks) on use of free tyrosine with retention of the same amino acid pattern. The tyrosine content in amino acid solutions for parenteral nutrition has therefore to date often been covered by the more soluble acetyltyrosine. Acetyltyrosine is, however, poorly metabolized by the human body [Magnusson et al. (1989) Metabolism 38:957-961] and this particularly applies to the neonatal body.

A preferred solution to the problem again consists of providing tyrosine in the form of an oligopeptide, in particular of a tri-or dipeptide. Examples of tripeptides are X'-Tyr-X, X'-X-Tyr and Tyr-X'-X. Examples of dipeptides are Tyr-X and X-Tyr. X and X' are any naturally occurring amino acids, and alanine and glycine are preferably used.

Provision of glutamine and tyrosine in the form of the rapidly metabolizable oligopeptides mentioned allows a thermally sterilized complete amino acid solution to be prepared with, at the same time, high stability and storability.

It has surprisingly emerged that a thermal sterilization is possible at higher sterilization temperatures than usual (>121° C.) with the same sterilization efficiency (defined by a constant F0 value) and with greater stability of the oligopeptides. The sterilization temperature is in this connection preferably ≧124° C. and particularly preferably ≧127° C. The pH is preferably between 5 and 6.5. It is possible to reduce the holding times for the thermal sterilization on use of higher temperatures. Under the preferred conditions, distinctly smaller amounts of degradation products are found in the sterilized product (example 3).

For total parenteral nutrition, the amino acid solution of the invention can be mixed before administration with other parenteral dietary components to give a composition which meets all the requirements for complete nutrition. The calorie requirement in relation to body weight is increased in premature infants and neonates, and small children, because of the growth phase, compared with adults. The neonatal body requires a daily dose of 80-190 kcal/kg, preferably 90-120 kcal/kg, and this range falls to 75-90 kcal/kg for small children over one year of age, and below this range for older children. It is to be preferred in this connection for the amino acids provided in the parenteral nutrition therapy to be intended exclusively for protein construction and necessary metabolic processes, and not to serve for the general energy intake. A complete parenteral nutrition therefore provides only about 10-20% of the energy as protein building blocks, with 30-60% being provided by carbohydrates, preferably glucose, and a further 30-50% by fats. Electrolytes, vitamins and trace elements complete the parenteral dietary composition.

It is known that amino acids cannot be stored together with fats and carbohydrates because of the stability problems arising. These components of the parenteral nutrition are therefore mixed together only shortly before the administration under sterile conditions. Such a mixing before administration is therefore particularly time-consuming. The problem has been solved by multichamber bags with peelable seals as described for example in EP 1396249. The use of such a system is also suitable for administering Neoven according to the present invention.

The invention is to be explained in more detail by means of the following examples.

EXAMPLE 1

The properties of the amino acid solution of the invention are indicated in the following table on the basis of a volume of 1000 ml. Possible ranges of amounts, preferred ranges of amounts, preferred daily dose and a specific example of the amounts are given.

| 1000 ml infusion solution: | Possible ranges of amounts | Preferred ranges of amounts | Preferred daily dose per kg | Example |
|---|---|---|---|---|
| L-Leucine | 5-20 g | 9-12 g | 150-610 mg | 10.8 g |
| L-Isoleucine | 3-8 g | 4-6 g | 90-250 mg | 4.8 g |
| L-Lysine | 5-15 g | 7-10 g | 150-450 mg | 8.6 g |
| L-Methionine | 1-3 g | 1.5-2.5 g | 30-90 mg | 2.0 g |
| L-Phenyl-alanine | 3-5 g | 3.3-4 g | 90-150 mg | 3.6 g |
| L-Threonine | 3-8 g | 5-6 g | 90-250 mg | 5.5 g |
| L-Tryptophan | 1-4 g | 1.5-2.8 g | 30-120 mg | 2.2 g |
| L-Valine | 3-8 g | 5-6 g | 90-250 mg | 5.5 g |
| L-Arginine | 3-12 g | 6-9 g | 90-370 mg | 8.0 g |
| L-Histidine | 1.5-6 g | 2-4 g | 45-180 mg | 3.2 g |
| L-Alanine | 5-15 g | 8-12 g | 150-450 mg | 9.7 g |
| Glycine | 1.5-6 g | 2.5-4 g | 45-180 mg | 3.2 g |
| Glycyl-L-tyrosine | 0.7-5 g | 2-3.3 g | 20-150 mg | 2.7 g |

-continued

| 1000 ml infusion solution: | Possible ranges of amounts | Preferred ranges of amounts | Preferred daily dose per kg | Example |
|---|---|---|---|---|
| L-Tyrosine | 1-4 g | 1.5-2.5 g | 30-120 mg | 2.0 g* |
| L-Proline | 5-15 g | 7-10 g | 150-450 mg | 8.6 g |
| L-Serine | 3-8 g | 4-6 g | 90-250 mg | 5.8 g |
| L-Cysteine (acetyl) | 0.3-1.5 g | 0.5-1 g | 9-45 mg | 0.7 g (1.0 g) |
| L-Alanyl-L-glutamine | 10-44 g | 17-30 g | 0.3-1.3 g | 22.0 g |
| L-Glutamine | 9-30 g | 11-20 g | 250-900 mg | 15.0 g** |
| L-Glutamic acid | 0-10 g | 0-3 g | 0-300 mg | 0 |
| Taurine | 0.3-2 g | 0.7-1.5 g | 9-60 mg | 1.0 g |
| AA g | 30-200 g | 80-150 g | 2-4 g | 100.5 g |
| EAA | 15-90 g | 30-60 g | 0.4-2.8 g | 43.0 g |
| BCAA | 7-40 g | 15-30 g | 0.2-1.2 g | 21.1 g |
| NEAA | 20-120 g | 45-80 g | 0.6-3.6 g | 57.5 g |
| N (nitrogen) | 4.8-32 | 12.8-24 | 0.32-0.64 | 16.0 g |
| pH | 5-7 | 5-6.5 | | 5.8-6.2 |
| Titration acidity [mmol NaOH] | <40 | <35 | | 30 |
| Osmolarity [mosmol/l] | 600-1000 | 700-900 | | 785 |

*in the form of L-alanyl-L-tyrosine
**in the form of glycyl-L-tyrosine
AA = amino acids
EAA = essential amino acids
BCAA = branched chain amino acids

EXAMPLE 2

A solution for complete parenteral nutrition of a pediatric patient comprises per kg of body weight for infusion of a daily dose over 24 hours:

| | | |
|---|---|---|
| 12-35 ml | Amino acid solution according to Example 1 | |
| 20-120 ml | 5-20% glucose solution | |
| 2-15 ml | Lipid solution | |
| 2-3 mmol | Sodium | |
| 2-3 mmol | Potassium | |
| 0.1-0.6 mmol | Calcium | |
| 0.1-0.8 mmol | Magnesium | |
| 0.5-15 µg | Vitamin D | |
| 2-7 mg | Vitamin E | |
| 10-200 µg | Vitamin K | |
| 10-80 mg | Vitamin C | |
| 0.3-1.5 mg | Vitamin B1 | |
| 0.1-1.5 mg | Vitamin B2 | |
| 0.1-1.5 mg | Vitamin B6 | |
| 0.2-1.2 µg | Vitamin B12 | |
| 4-18 mg | Niacin | |
| 50-150 µg | Folic acid | |
| 50-500 µg | Zinc | |
| 2-3 µg | Selenium | |
| 30-200 µg | Iron | |

EXAMPLE 3

A solution of 200 g/l alanyl-glutamine was sterilized at temperatures of 121° C., 124° C. and 127° C. The pH was varied between pH 5, pH 5.5 and pH 6. The holding times for the thermal sterilization were varied so that comparable F0 values between 12 and 12.5 were reached, demonstrating that the sterilization efficiency remains at the same level. The F0 value describes the sterilization efficiency and corresponds to the holding time at 121.11° C. For sterilization at higher temperatures, the holding times were reduced to maintain a constant F0 value. After the sterilization, the amounts of the degradation products of the dipeptide alanyl-glutamine, cyclo-alanyl-glutamine and L-pyro-alanyl-glutamine were determined. Lower values for these degradation products are a direct indication of the stability of the dipeptide during the sterilization. The values for the degradation products fell at higher temperature.

The results of the sterilization tests are shown in the following table.

| pH | $T_{st}$ | c-ala-gln [%] | pyro-glu-ala [%] | F0 |
|---|---|---|---|---|
| 5.0 | 121° C. | 1.09 | 0.36 | 12.1 |
| 5.5 | 121° C. | 1.31 | 0.30 | 12.1 |
| 6.0 | 121° C. | 1.54 | 0.28 | 12.1 |
| 5.0 | 124° C. | 0.89 | 0.30 | 12.5 |
| 5.5 | 124° C. | 1.08 | 0.26 | 12.5 |
| 6.0 | 124° C. | 1.25 | 0.24 | 12.5 |
| 5.0 | 127° C. | 0.76 | 0.26 | 12.5 |
| 5.5 | 127° C. | 0.9 | 0.22 | 12.5 |
| 6.0 | 127° C. | 1.08 | 0.21 | 12.5 |

EXAMPLE 4

A solution for parenteral administration is provided in a two-chamber bag with peelable partition. One chamber of the bag contains the amino acid solution of the invention and the other chamber contains a nutritional solution comprising glucose, electrolytes, vitamins and trace elements. The composition is particularly suitable for pediatric patients from one month to one year of age.

| Composition | Preferred range | Specific example |
|---|---|---|
| Volume in ml | 100 | 100.0 |
| AA g (of Ex. 1) | 2-3 | 2.4 |
| Glucose g | 9-15 | 12.0 |
| Na mmol | 2-3 | 2.40 |
| K mmol | 1.5-2.5 | 2.00 |
| Ca mmol | 1-1.8 | 1.44 |
| Mg mmol | 0.1-0.3 | 0.20 |
| P mmol | 0.9-1.4 | 1.12 |

Bags with corresponding compositions are available in sizes of 350 ml, 500 ml and 1000 ml in order to provide patients of different age groups with an appropriate amount.

EXAMPLE 5

A solution for parenteral administration is provided in a three-chamber bag with peelable partition. One chamber of the bag contains the amino acid solution of the invention, one chamber contains a nutritional solution comprising glucose, electrolytes, vitamins and trace elements. A further chamber comprises a lipid emulsion. The lipid emulsion preferably comprises fats from soybean oil, medium-chain fatty acids (MCT), olive oil and fish oil. The composition is particularly suitable for pediatric patients with a weight of 10-40 kg and over one year of age. However, it can also generally be assumed to be suitable for younger patients.

| Composition | Preferred range | Specific example |
|---|---|---|
| Volume ml | 100 | 100 |
| Total calories | 60-100 | 80 |
| AA g (of Ex. 1) | 1.5-2.5 | 2 |
| Glucose g | 9-15 | 12 |
| Fats g (SMOFlipid) | 1.5-2.5 | 2 |
| Na mmol | 2-2.5 | 2.22 |
| K mmol | 2-2.5 | 2.22 |
| Ca mmol | 0.4-0.7 | 0.56 |
| Mg mmol | 0.05-0.15 | 0.11 |
| P mmol | 0.6-1 | 0.78 |

Bags with corresponding compositions are available in sizes of 1000 ml and 2000 ml in order to provide patients of different weight classes with an appropriate amount.

The invention claimed is:

1. A solution for parenteral nutrition of pediatric patients, characterized in that the solution comprises 1-4 g tyrosine per 100 g of amino acids, 3-5 g phenylalanine per 100 g of amino acids, 0.3-1.5 g cysteine per 100 g of amino acids, 1-3 g methionine per 100 g of amino acids, 9-30 g glutamine per 100 g of amino acids and 0.3-2 g taurine per 100 g of amino acids.

2. The solution according to claim 1, further comprising glutamine in the form of oligopeptides.

3. The solution according to claim 1, further comprising tyrosine in the form of oligopeptides having a chain length of at most 5 amino acid units.

4. The solution according to claim 2, wherein the oligopeptides are dipeptides or tripeptides.

5. The solution according to claim 2, wherein the glutamine in the form of oligopeptides is present in the form of alanyl glutamine, glycyl glutamine or mixtures thereof.

6. The solution according to claim 3, wherein the tyrosine in the form of oligopeptides is present in the form of glycyl tyrosine, alanyl tyrosine or mixtures thereof.

7. The solution according to claim 1, wherein the solution contains at most 3 g/l glutamic acid.

8. The solution according to claim 1, wherein the solution comprises 3-30% w/w protein building blocks.

9. The solution according to claim 1, wherein the ratio of tyrosine to phenylalanine is from 1:1 to 1:3.

10. The solution according to claim 1, wherein the combined amount of the amino acids cysteine, taurine and methionine is 2-5% of all amino acids.

11. The solution according to claim 1, wherein the solution contains less than 1% proteins or peptides having a chain length >5 amino acid units.

12. A medical composition for complete parenteral nutrition, comprising:
  a) the solution according to claim 1,
  b) carbohydrates, and
  c) fats,
    wherein said solution, said carbohydrates and said fats each provide enerqy upon consumption,
    wherein the solution provides 10-20% of the total energy, the carbohydrates provide 30-60% of the total energy, and the fats provide 30-50% of the total energy provided by the composition, and
    wherein the proportions of energy provided by the solution, the carbohydrates and the fats add up to 100%.

13. The medical composition according to claim 12, additionally comprising electrolytes, vitamins and trace elements.

14. A method of preparing a sterile solution, comprising:
  preparing the solution according to claim 1, wherein the 9-30 g glutamine per 100 g of amino acids in the form of oligopeptides, and
  thermally sterilizing the solution at a temperature of ≧124° C.

15. A method of providing parenteral nutrition to a pediatric patient suffering from at least one selected from malformation of the bowel, inflammation of the bowel, a renal disorder and a hepatic disorder, the method comprising:
  administering to a patient in need thereof the solution according to claim 1.

16. The medical composition according to claim 12, wherein the medical composition is a parenteral infusion solution for administration to pediatric patients comprising a daily dose of 90-180 kcal/kg body weight of the patient.

* * * * *